United States Patent [19]

Miller et al.

[11] Patent Number: 5,334,777

[45] Date of Patent: Aug. 2, 1994

[54] CONVERSION OF ALKANES TO ALKANOLS AND GLYCOLS

[75] Inventors: Jorge Miller; Miguel Kling, both of Bogota, Colombia

[73] Assignee: Energia Andina Ltd., New York, N.Y.

[21] Appl. No.: 101,739

[22] Filed: Aug. 4, 1993

Related U.S. Application Data

[63] Continuation-in-part of Ser. No. 971,899, Nov. 4, 1992, Pat. No. 5,243,098.

[51] Int. Cl.$^5$ .................. C07C 27/00; C07C 29/00; C07C 31/18
[52] U.S. Cl. ................... 568/859; 422/142; 502/225
[58] Field of Search .......................................... 568/859

[56] References Cited

U.S. PATENT DOCUMENTS

| | | | |
|---|---|---|---|
| 1,594,608 | 8/1926 | Essey et al. | 568/859 |
| 2,181,297 | 11/1939 | Britton et al. | 568/859 |
| 5,243,098 | 9/1993 | Miller et al. | |

FOREIGN PATENT DOCUMENTS 2633228 2/1977 Fed. Rep. of Germany ...... 568/859

569717 6/1945 United Kingdom ............... 568/859

Primary Examiner—Johann Richter
Assistant Examiner—Rebecca Cook
Attorney, Agent, or Firm—Jacobson, Price, Holman & Stern

[57] ABSTRACT

Lower monobasic or dibasic alcohols are produced by the following steps:

a) reacting a starting material with a metallic halide (wherein the metal is in the higher of two possible valence states) to obtain a reaction product, a corresponding metallous halide (wherein the metal is in the lower of the two possible valence states) and hydrohalic acid, and b) reacting the reaction product of step (a) and hydrohalic acid with magnesium oxide to form the corresponding lower monobasic or dibasic alkanol;

wherein the starting material for forming a lower monobasic alcohol is a lower alkane, from which the corresponding lower alkanol is obtained; and the starting material for forming a lower dibasic alcohol is either a lower alkanol or a lower alkene, from which the corresponding lower glycol is obtained. Two continuous fluidized-bed systems are provided for conducting the necessary reactions.

11 Claims, 2 Drawing Sheets

CONVERSION OF ALKANES TO ALKANOLS AND GLYCOLS

RELATED APPLICATION

This application is a continuation-in-part of application Ser. No. 07/971,899, filed Nov. 4, 1992 now U.S. Pat. No. 5,243,098.

FIELD OF THE INVENTION

A lower alkane is reacted with a metal chloride to produce the corresponding alkyl chloride, Reacting the obtained alkyl chloride with magnesium oxide and steam yields the corresponding alkanol. In a similar fashion lower alkanes are converted to corresponding glycols.

BACKGROUND

Methane has previously been chlorinated with gaseous chlorine or subjected to oxychlorination with oxygen and hydrochloric acid to form methyl chloride together with other chlorides, such as dichloromethane, trichloromethane and carbon tetrachloride- In the halogenation of methane by either method, hydrochloric acid is produced. Such hydrochloric acid must be recovered, dehydrated by azeotropic distillation and recycled.

Reduced chloromethanes are then hydrolyzed in vapor phase to methanol, formaldehyde, formic acid, carbon dioxide and hydrochloric acid. Resulting compositions depend on the chlorination selectivity to methyl chloride and to other chlorides. Corrosion and problems involved with handling chlorine and hydrochloric acid are substantial.

SUMMARY OF THE INVENTION

An object of the invention is to overcome or eliminate previously-encountered problems and to obtain a simplified process for converting an alkane to the corresponding alkanol. The method is based on the formation of an alkyl chloride and its hydration to the corresponding alcohol.

According to this process, methane (the preferred alkane) is reacted with a metal halide (metallic halide), wherein the metal is in the higher of two possible valence states, to form methyl halide, the corresponding metal halide (metallous halide), wherein the metal is in the lower of two possible valence states, and hydrohalic acid. The obtained methyl halide and hydrohalic acid are reacted with magnesium oxide to form methyl alcohol and magnesium halide hydrate. The obtained metallous halide is reacted with hydrohalic acid and oxygen to form metallic halide, and the magnesium halide hydrate is converted to magnesium oxide and hydrohalic acid. Lower alkenes are similarly converted to corresponding glycols.

DETAILS

Figure 1:
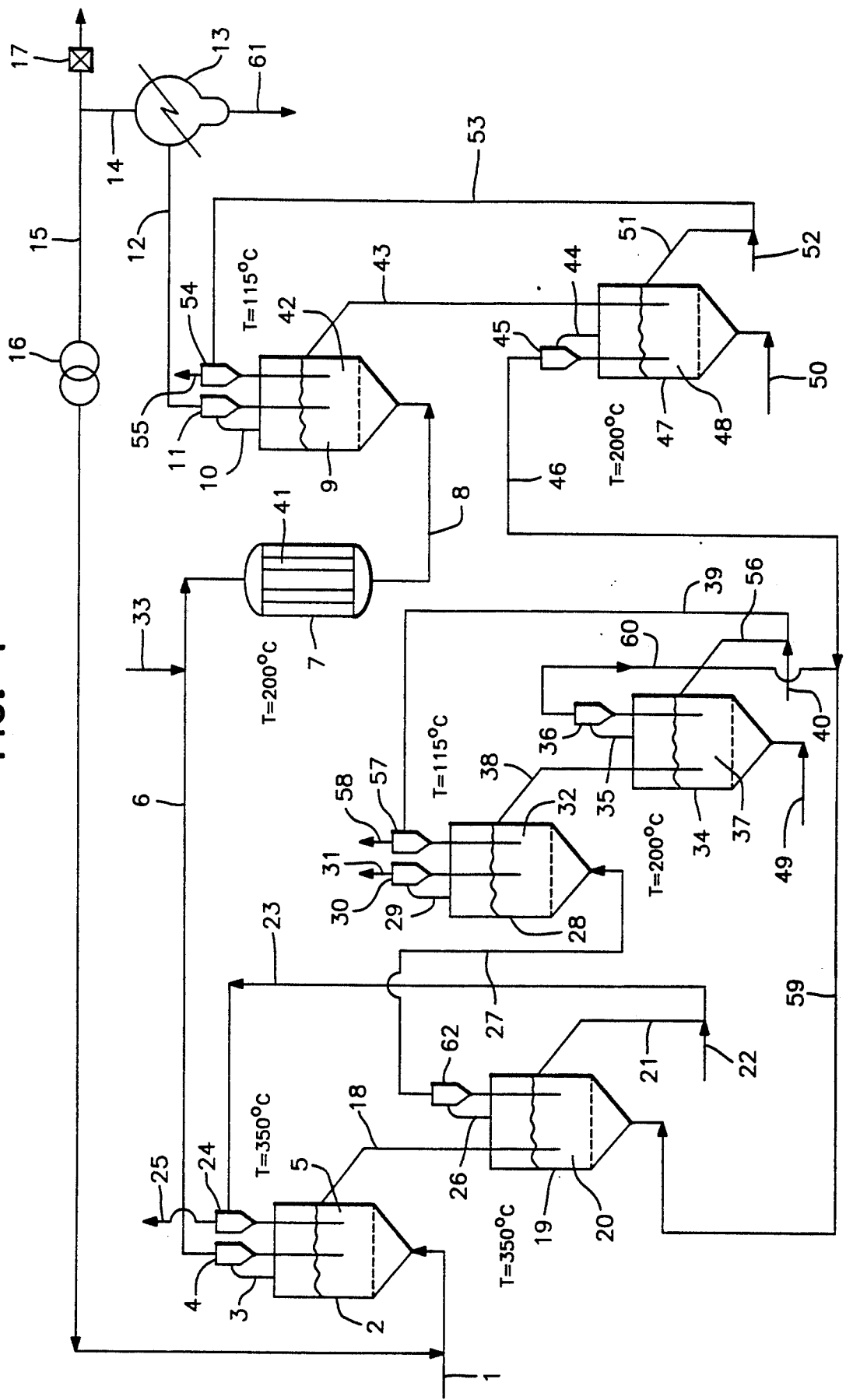
FIG. 1 is a flow diagram depicting one embodiment of the claimed process.

Methane is reacted with a metal chloride which is capable of chlorinating methane. The metal is one which concurrently reduces its valence to a lower state. For example, cupric chloride reacts with methane to form methyl chloride, cuprous chloride and hydrochloric acid, according to reaction (I)

$$2\ CuCl_2 + CH_4 \rightarrow 2CuCl + CH_3Cl + HCl \quad (I)$$

The obtained methyl chloride and hydrochloric acid are next reacted with steam and a catalyst containing magnesium oxide, according to reaction scheme (II)

$$H_2O + CH_3Cl + HCl + MgO \rightarrow CH_3OH + MgCl_2 + H_2O \quad (II)$$

Air and oxygen are passed countercurrent through the magnesium chloride to recover hydrochloric acid according to reaction scheme (III)

$$MgCl_2 \cdot xH_2O \rightarrow MgO + 2HCl \quad (III)$$

and then through the cuprous chloride to reform cupric chloride according to reaction scheme (IV)

$$2HCl + \tfrac{1}{2}O_2 + 2CuCl \rightarrow 2CuCl_2 + H_2O \quad (IV).$$

Reaction (I) is advantageously carried out at temperatures between 300° C. and 360° C., at which temperatures there is no formation of chlorine by decomposition of cupric chloride. Such decomposition takes place at 993° C. to yield chlorine. By keeping the temperature low, the possibility of overchlorination of the methyl chloride to higher chlorides is minimized.

Reaction (II) is advantageously conducted at 200° C. or less in order to avoid adsorbing chlorides and to release them according to the law of mass action.

Reaction (III) is advantageously carried out at about 200° C., and reaction (IV) is advantageously carried out within the approximate range of from 300° C to 380° C.

The preferred method is a continuous process, using fluidized-bed reactors. However, fluidized bed reactors are not necessary, and batch reactions can be employed. Instead of a metal chloride, such as copper chloride, in reaction (I), a mixture can be employed. The preferred mixture is one of cupric chloride, cuprous chloride and magnesium oxide. This particular mixture is preferably used for chlorination of methane because, by diluting the copper chloride with magnesium oxide, less higher methyl chlorides are formed. Also, when reoxidizing in the presence of hydrochloric acid, the magnesium chloride formed reacts with any copper oxide formed to produce copper chloride. Magnesium oxide also serves to increase porosity.

$$MgCl_2 + CuO \rightarrow MgO + CuCl_2 \quad (V)$$

Excess cuprous chloride adsorbs any formed chlorine.

$$CuCl + \tfrac{1}{2}Cl_2 \rightarrow CuCl_2 \quad (VI)$$

Instead of reacting methyl chloride with magnesium oxide in reaction (II), a magnesium zeolite can be used to hydrolyze the methyl chloride to methanol and hydrochloric acid; at 200° C. the hydrochloric acid is next adsorbed by magnesium oxide. At temperatures in excess of 115° C., $MgCl_2 \cdot 4H_2O$ is formed, completely adsorbing all of the hydrochloric acid, which can be recovered by heating to 200° C., while passing air therethrough.

The mechanism and kinetics of the thermal decomposition of magnesium chloride hydrates have been reported (Kirk-Othmer Encyclopedia of Chemical Technology, Vol. 14–623, Third Edition). The reactions which are reversible take place in stages as shown.

$$95° C.-115° C. MgCl_2.6H_2O \rightleftharpoons MgCl_2.4H_2O + 2 H_2O$$

$$135° C.-180° C. MgCl_2.4 H_2O \rightleftharpoons Mg(OH) + HCl + 3 H_2O$$

$$186° C.-230° C. MgCl_2.H_2O \rightleftharpoons Mg(OH) Cl + HCl$$

Advantage is taken of these properties of magnesium chloride hydrates to adsorb and recover hydrochloric acid.

The exceedingly high conversion of methyl chloride to methyl alcohol (practically 100%), by the magnesium form of the zeolite ($Mg Z_2$), can be attributed to the following reactions:

$$MgZ_2 + 2CH_3Cl \rightarrow MgCl_2 + 2CH_3Z$$

$$CH_3Z + H_3O \rightarrow HZ + CH_3OH$$

and $$MgCl_2 + H_2O \rightarrow Mg(OH)_2 + 2HCl$$

$$Mg(OH)_2 + 2HZ \rightarrow MgZ_2 + 2H_2O$$

In this case the magnesium zeolite acts like a catalyst.

With reference to FIG. 1, which depicts a typical continuous process using fluidized reactors, methane is introduced to fluid bed fluidizer 2 through line 1, where it reacts with cupric chloride contained in fluidized reactant 5, composed of a mixture of magnesium oxide, cupric chloride and cuprous chloride. (Alternatively, cupric bromide and cuprous bromide can be used). The reacted gas, comprising mostly hydrochloric acid, methyl chloride and excess methane, flows through line 3 to cyclone 4, which returns dust to reactor 2. Gas, leaving cyclone 4 through line 6, enters reactor 7, which contains catalyst (magnesium zeolite) 41, together with steam provided through line 33. Reacted gases, comprising methyl alcohol, hydrochloric acid and excess methane, leave reactor 7 through line 8, which delivers them to fluidizer 9, containing magnesium oxide 42, which adsorbs all the hydrochloric acid.

Gases leaving fluidizer 9 through line 10 to cyclone 11, which returns dust to fluidizer 9, contain methyl alcohol and excess methane. These gases are led through line 12 to condenser 13, where methyl alcohol is condensed and leaves condenser 13 through line 61.

Non-condensed methane leaves condenser 13 through line 14 to bleed valve 17 and through line 15 to compressor 16, which recirculates excess methane to line 1.

Spent reactant 5 from fluidizer 2 flows through line 18 to fluidizer 19, where it meets a flow of gas containing air and hydrochloric acid; cuprous chloride therein is regenerated back to cupric form.

Regenerated reagent 20 flows through line 21, where it meets conveying gas air 22, which lifts it through line 23 to cyclone 24, where conveying gas (air) is exhausted through line 25 to the atmosphere and reagent 5 is delivered by cyclone 24 to fluidizer 2.

Gases from fluidizer 19, containing possible traces of hydrochloric acid, are led through line 26 to cyclone 62, returning dust to fluidizer 19 and delivering gases through line 27 to fluidizer 28, which contains magnesium oxide 32, which adsorbs all traces of hydrochloric acid. The purified gas is bled to the atmosphere through line 29 and cyclone 30, which returns dust to fluidizer 28 and exhausts clean gas, free of pollution, through line 31.

Spent magnesium oxide 32 leaves fluidizer 28 through line 38, which delivers it to fluidizer 34, where it meets a flow of air, which regenerates the spent magnesium oxide 37. Regenerated magnesium oxide is conducted through line 56, where a conveying gas 40 lifts it through line 39 to cyclone 57. Conveying gas is exhausted through line 58 to the atmosphere, and regenerated magnesium oxide is delivered to fluidizer 28. Gases leaving fluidizer 34, containing air and hydrochloric acid, are led through line 35 to cyclone 36, where dust is returned to fluidizer 34, and gases are led through line 60 to line 59.

Spent magnesium oxide 42 leaves fluidizer 9 through line 43, which delivers it to fluidizer 47, where it meets a flow of air, introduced through line 50, which regenerates the spent magnesium oxide 48. Regenerated magnesium oxide flows through line 51, where it meets a conveying gas (air) 52, which lifts it to cyclone 54 through line 53. Conveying gas is exhausted through line 55, and cyclone 54 delivers regenerated magnesium oxide to fluidizer 9.

Gases leaving fluidizer 47, containing hydrochloric acid and air, are delivered through line 44 to cyclone 45, where dust is returned to fluidizer 47, and gases are led through line 46 to line 59 and, together with gases from line 60, enter fluidizer 19.

Air enters fluidizer 34 through line 49; air enters fluidizer 47 through line 50.

Temperatures indicated in FIG. 1 are indicative. Reactant 5 is made, e.g., by mixing cuprous chloride, cupric chloride and magnesium oxide, the molar proportions suggested are:
cupric chloride 1 mole
cuprous chloride 0.1 mole
magnesium oxide 2 moles
The reagent is advantageously made as follows:

1.1 mole of cupric chloride is dissolved in water to saturation. 2 moles of magnesium oxide are added. The mixture is evaporated to dryness and granulated.

The granulated product is then reduced with methane or hydrogen until 0.1 mole of copper chloride is reduced to cuprous chloride. When regenerating the reagent, cuprous chloride must always be present.

Magnesium oxide serves to tone down the activity of the cupric chloride. Other diluent materials can be used in combination with magnesium oxide (aluminum oxide, silica, fullers earth, etc.).

When conversion per pass is limited to less than 20%, overchlorination of the methane is limited to less than 1%. Increasing magnesium oxide in the reagent also has the same effect.

Magnesium zeolite catalyst is preferably prepared as follows: Type A or Type X zeolite, as defined in "Kirk-Othmer Encyclopedia of Chemical Technology" 3d Edition, Vol. 15, Page 665, is placed in a column, and a solution of soluble magnesium salt (sulfate, nitrate, etc.) is passed through the zeolite, whereby sodium is exchanged for magnesium. The zeolite in the magnesium form is then washed and dried, ready for use. The process is well known ("Kirk-Othmer Encyclopedia of Chemical Technology" 3d Edition, Vol. 13, page 678, etc.).

Although the preceding illustration has been made with copper chlorides, such chlorides are optionally replaced with bromides. Also, methane is optionally replaced with ethane, propane or n-butane to produce corresponding alcohols.

Figure 2:
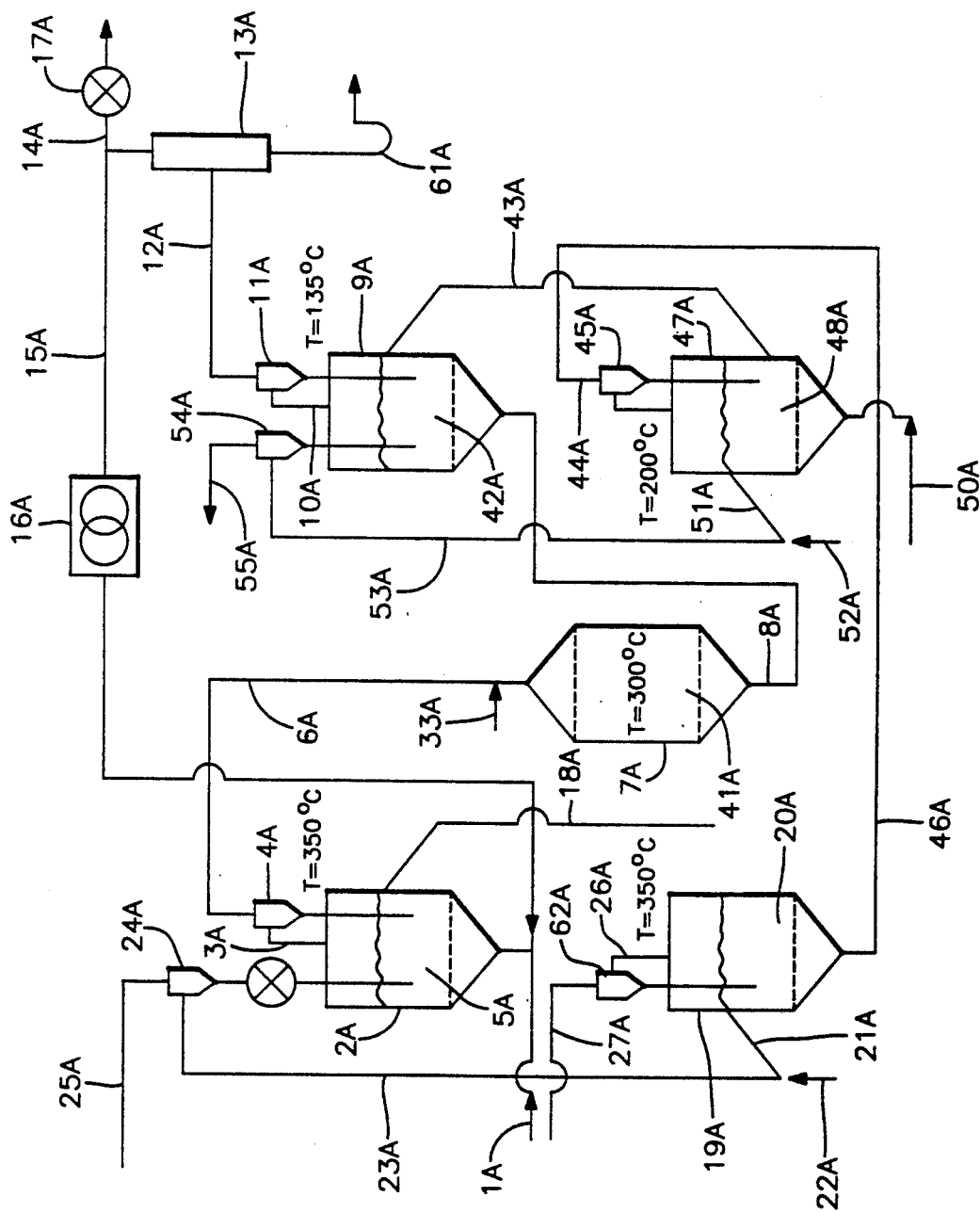
FIG. 2 is a flow diagram depicting a second and simplified embodiment of the claimed process.

An alternative embodiment (FIG. 2) omits fluidizer 28 and fluidizer 34 of FIG. 1. In FIG. 2 corresponding equipment is designated by similar numbers with an A suffix for ease of comparison. All of the hydrochloric acid from fluidizer 47A is completely absorbed in reactor 19A without forming chlorine.

A careful thermodynamic analysis of the reactions involves the following:

| REACTION CONSTANTS (T = 300 K.°) | | |
|---|---|---|
| $2HCl + \frac{1}{2}O_2 \rightarrow Cl_2 + H_2O$ | $\Delta F = -9080$ cal | $K = 9.35 \times 10^6$ |
| $2CuCl + \frac{1}{2}O_2 \rightarrow CuCl_2 + CuO$ | $\Delta F = -15700$ cal | $K = 3.01 \times 10^{11}$ |
| $CuO + HCl \rightarrow CuCl_2 + H_2O$ | $\Delta F = -42857$ cal | $K = 2.16 \times 10^{31}$ |

The ease of reaction depends on the reaction constant K; thus, long before any chlorine is formed from the oxidation of the hydrochloric acid, it reacts with the copper oxide present.

In order to insure this, an excess of copper oxide is incorporated in the original reaction mixture. The preferred composition of reactant 5 contains at least 0.1 mole of copper oxide in addition to magnesium oxide and cuprous chloride, e.g.,
cupric chloride: 1 mole
cupric oxide: 0.1 mole
cuprous chloride: 0.1 mole
magnesium oxide: 2 moles FIG. 2 illustrates a simplified configuration of FIG. 1, wherein a lower alkane is converted to a corresponding lower alkanol in a manner corresponding to that disclosed with regard to FIG. 1, but with the inclusion of metallic oxide, e.g. cupric oxide, in reactant 5.

When a lower alkene, e.g. ethylene, is processed in the same equipment under corresponding conditions, it is first chlorinated to 1,2-dichloroethane and hydrolyzed to ethylene glycol. The only difference is that a larger proportion of steam is required to prevent its condensation in reactor 7A along with a higher temperature in fluidizer 9A (135° C.). The following data show the vapor pressures versus temperatures for ethylene glycol.

| Vapor Pressure (mm Hg) | Temperature (°C.) |
|---|---|
| 10 | 92.1 |
| 20 | 105.8 |
| 40 | 120.0 |
| 60 | 129.5 |
| 100 | 141.8 |
| 200 | 158.5 |
| 400 | 178.5 |
| 760 | 197.3 |

Thus, if the partial pressure of ethylene glycol is 80 mmHg, in view of excess steam and excess ethylene, the temperature in fluidizer 9A can be held at 135° C.

When ethyl alcohol is vaporized and similarly processed in the same equipment, it is first chlorinated to ethylene chlorohydrin, which is hydrolyzed in turn to ethylene glycol. The same temperature precautions are observed.

With reference to FIG. 2, which depicts a typical continuous process using fluidized reactors, ethylene is introduced to fluidized bed reactor 2A through line 1A, where it reacts with cupric chloride contained in fluidized reactant 5A, composed of a mixture of cupric chloride, cupric oxide, magnesium oxide, and cuprous chloride. Alternatively, bromides are used instead of chlorides.

The reacted gas, comprised mostly of hydrochloric acid, 1,2-dichloroethane and excess ethylene, flows through line 3A to cyclone 4A, which returns dust to reactor 2A. Gas, leaving cyclone 4A through line 6A, enters reactor 7A, which contains catalyst 41A (magnesium zeolite), together with steam provided through line 33A. Reacted gases, comprising ethylene glycol, hydrochloric acid and excess methane, leave reactor 7A through line 8A, which delivers them to fluidizer 9A, containing magnesium oxide 42A, which absorbs all of the hydrochloric acid. Gases leaving fluidizer 9A through line 10A to cyclone 11A, which returns dust to fluidizer 9A, contain ethylene glycol, excess ethylene, and water vapor. These gases are led through line 12A to condenser 13A, where glycol and water vapor are condensed, and leave condenser 13A through line 61A.

Non-condensed ethylene leaves condenser 13A through line 14A to bleed valve 17A and through line 15A to compressor 16A, which recirculates excess ethylene to line 1A.

Spent reactant 5A from fluidizer 2A flows through line 18A to fluidizer 19A, where it meets a flow of gas containing air and hydrochloric acid; cuprous chloride therein is regenerated back to cupric form.

Regenerated reagent 20A flows through line 21A, where it meets conveying gas (air) 22A, which lifts it through line 23A to cyclone 24A, wherein conveying gas (air) is exhausted through line 25A to the atmosphere, and reagent 5A is delivered by cyclone 24A to fluidizer 2A.

Spent magnesium oxide 42A leaves fluidizer 9A through line 43A, which delivers it to fluidizer 47A, where it meets a flow of air introduced through line 50A, which regenerates the spent magnesium oxide 48A. Regenerated magnesium oxide flows through line 51A, where it meets a conveying gas (air) 52A, which lifts it to cyclone 54A through line 53A. Conveying gas is exhausted through line 55A, and cyclone 54A delivers regenerated magnesium oxide to fluidizer 9A.

Gases leaving fluidizer 47A, containing hydrochloric acid and air, are delivered through line 44A to cyclone 45A, where dust is returned to fluidizer 47A, and gases are led through line 46A to fluidizer 19A.

Air enters fluidizer 47A through line 50A. Temperatures indicated in FIG. 2 are indicative. Reactant 5A contains an excess of copper oxide.

Propylene glycol is similarly produced from propylene.

When ethyl alcohol, instead of ethylene, is the starting material for producing ethylene glycol, the condensed alcohol, water vapor, and glycol obtained in condenser 13A are sent to a splitter (not shown), where excess ethanol is separated from the glycol, and returned, vaporized, to line 1A.

The process and equipment disclosed are thus advantageously useful for converting lower alkanes to corresponding lower alkanols and for converting lower alkenes or lower alkanols to corresponding glycols.

The invention and its advantages are readily understood from the preceding description. It is apparent that various changes may be made in the process, in the system and in the compositions, without departing from the spirit and the scope of the invention or sacrificing its material advantages. The process, systems and products hereinbefore described are merely illustrative of preferred embodiments of the invention.

What is claimed is:

1. A process for producing a glycol from a corresponding lower alkene or lower alkanol which comprises the following steps:

a) reacting the alkene or alkanol with a metal halide (wherein the metal is in the higher of two possible valence states) to form a corresponding alkyl dihalide or halo alcohol, the corresponding metal halide (wherein the metal is in the lower of the two possible valence states), and hydrohalic acid; and b) reacting the obtained hydrohallo acid and alkyl dihalide or halo alcohol with magnesium oxide and $H_2O$ to form the corresponding glycol and magnesium halide hydrate.

2. A process of claim 1 wherein the metal is copper.

3. A process of claim 1 wherein the halide is chloride.

4. A process of claim 1 which is substantially conducted in a fluidized bed.

5. A process of claim 4, a fluidized bed of which comprises a mixture of cupric chloride, cuprous chloride and magnesium oxide.

6. A process of claims 5 wherein the mixture comprises cupric chloride, cuprous chloride, cupric oxide and magnesium oxide.

7. A process of claim 1 wherein a lower alkene is reacted with a metal halide.

8. A process of claim 7 wherein the lower alkene is ethylene.

9. A process of claim 7 wherein the lower alkene is propylene.

10. A process of claim 1 wherein a lower alkanol is reacted with a metal halide.

11. A process of claim 10 wherein the lower alkanol is ethanol.

* * * * *